United States Patent [19]

Cole et al.

[11] Patent Number: 5,697,910
[45] Date of Patent: Dec. 16, 1997

[54] REUSABLE CARTRIDGE ASSEMBLY FOR A PHACO MACHINE

[75] Inventors: Mark S. Cole, Canyon; Edward R. Zaleski, Santa Ana, both of Calif.

[73] Assignee: Allergan, Waco, Tex.

[21] Appl. No.: 608,578

[22] Filed: May 17, 1996

Related U.S. Application Data

[63] Continuation-in-part of Ser. No. 276,085, Jul. 15, 1994, Pat. No. 5,533,976.
[51] Int. Cl.$^6$ ............................................. A61M 1/00
[52] U.S. Cl. ........................................ 604/153; 604/65
[58] Field of Search .................... 604/30–34, 65–67, 604/153; 128/DIG. 12, 13

[56] References Cited

U.S. PATENT DOCUMENTS 5,324,422  6/1994  Colleran .................... 210/85

FOREIGN PATENT DOCUMENTS

| 0559602 | 8/1993 | European Pat. Off. . |
|---|---|---|
| 9312825 | 8/1993 | WIPO . |
| 8324817 | 12/1993 | WIPO . |
| 9328874 | 12/1993 | WIPO . |
| 9415099 | 7/1994 | WIPO . |

*Primary Examiner*—Manuel Mendez
*Attorney, Agent, or Firm*—Walter A. Hackler

[57] ABSTRACT

A reusable cartridge assembly for a phaco machine includes a plurality of flexible tubes for handling of irrigation and aspiration fluids to and from a handpiece. A plate having a plurality of channels formed therein supports and removably holds the flexible tubes within said plate. Apertures in said plate aligned with said channel means are provided for enabling plunger access to the flexible tubes in order to regulate fluid flow therethrough.

22 Claims, 5 Drawing Sheets

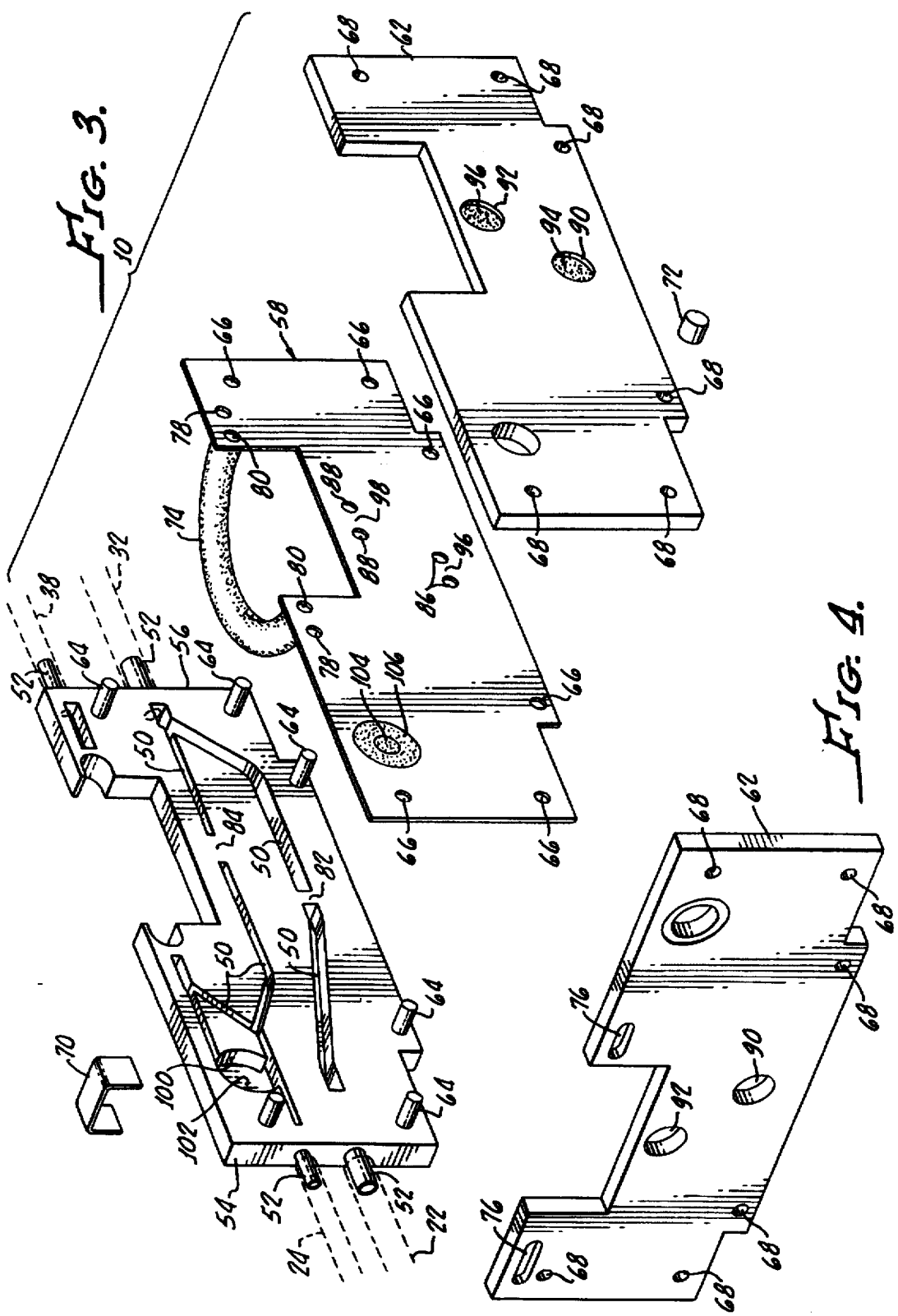

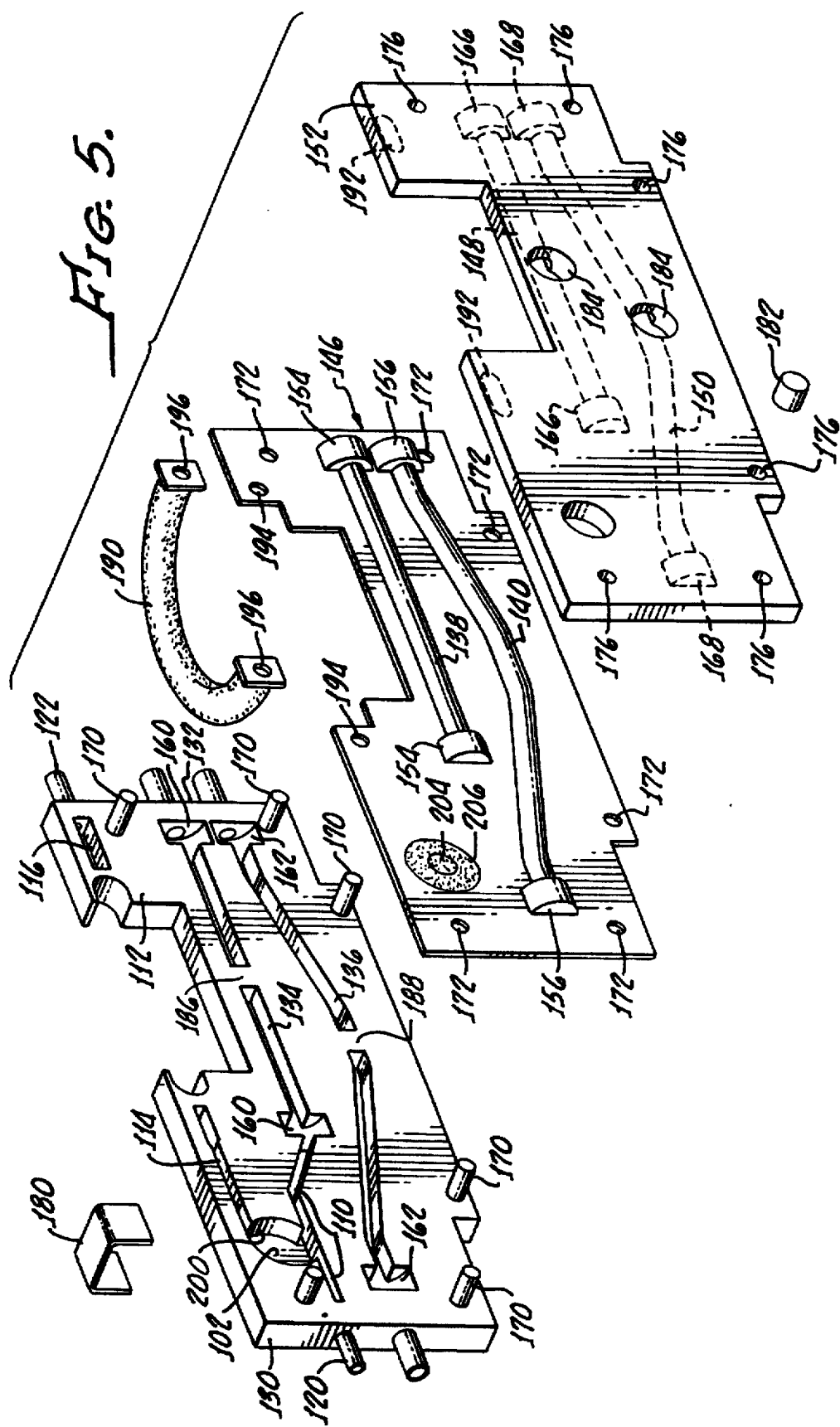

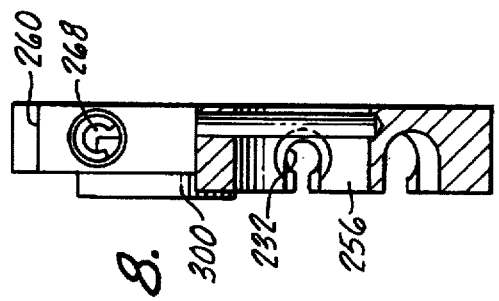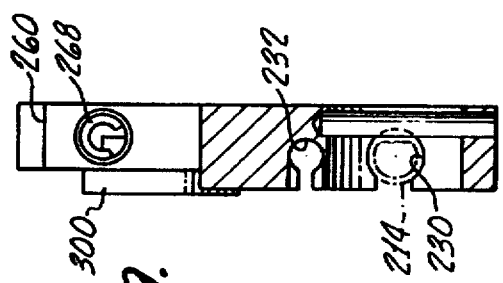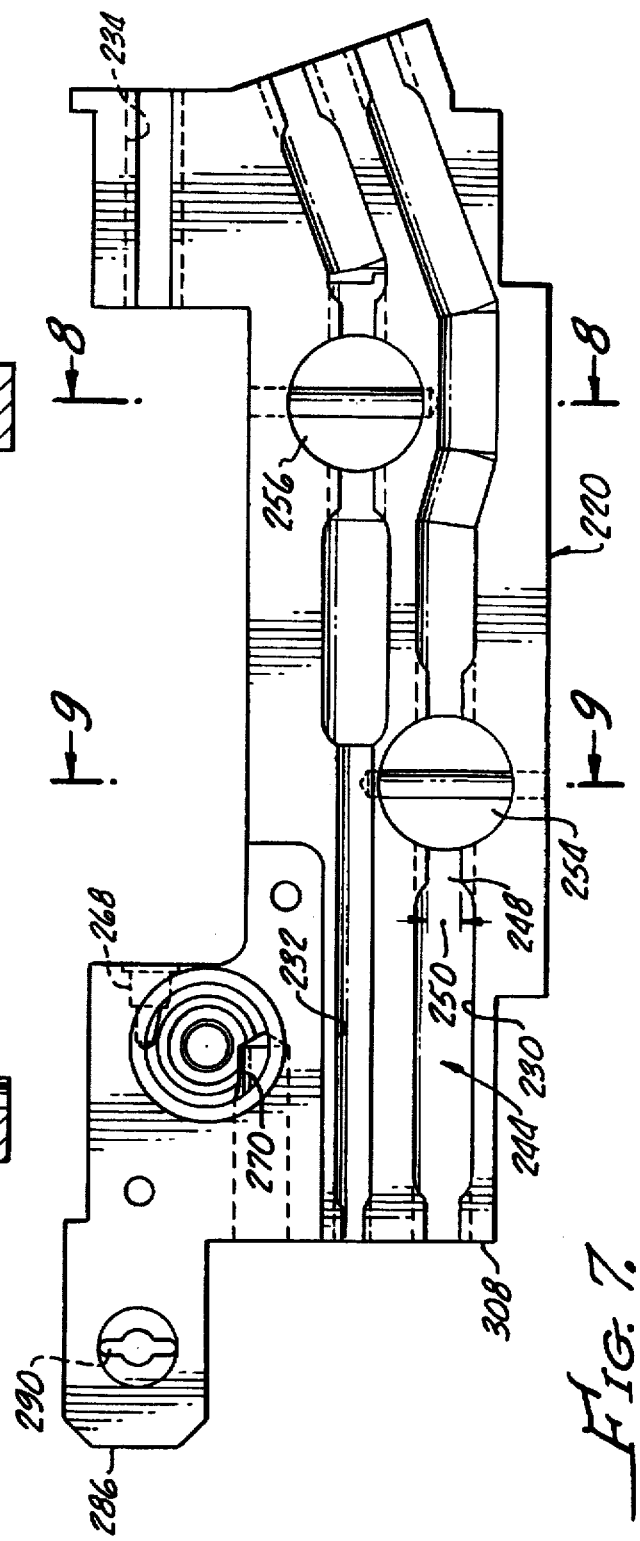

REUSABLE CARTRIDGE ASSEMBLY FOR A PHACO MACHINE

The present application is a continuation-in-part of U.S. patent application Ser. No. 08/276,085 filed Jul. 15, 1994, now U.S. Pat. No. 5,533,976.

The present invention generally relates to irrigation/ aspiration apparatus for surgical procedures and more particularly relates to a cartridge assembly for a drawer-loaded cassette system for use with a surgical instrument for endophthalmic surgery.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced salt solution is supplied from an elevated chamber, the chamber being elevated to a position to provide proper head, or pressure.

The irrigation and aspiration of fluid through the eye must be carefully monitored in order to maintain normal pressure within the eye during surgical procedures. An under-pressure may cause distortion of the eye which often may interfere with surgical procedures. Over pressure may cause damage to the eye and in extreme cases, rupture thereof.

As it has been hereinabove noted, pressure in the eye may be controlled by the physical elevation of the chamber of balanced salt solution, which is connected to the surgical instrument. Aspiration fluid, on the other hand, is controlled in the eye with a peristaltic pump.

Typical apparatus includes instrument console for controlling the flow of fluids. Various devices have been developed for the coordinated flow of fluids and some include a phacocassette, tubing and management system, which may be disposable or autoclavable, for interconnecting from the various tubes and lines for proper irrigation and aspiration.

A general discussion of the advantages of this type of cassette is set forth in U.S. Pat. No. 4,713,051. Further descriptions of phaco apparatus are disclosed in copending U.S. patent applications, Ser. Nos. 08/105,461 and 08/201, 567, these disclosures being incorporated into the present application in toto by this specific reference thereto.

SUMMARY OF THE INVENTION

A reusable cartridge assembly in accordance with the present invention for a phaco machine generally includes a plurality of flexible tubes for handling the irrigation and aspiration of fluids to and from a phaco handpiece. A plate is provided, along with channel means formed in the plate, for supporting and removably holding the flexible tubes within the plate.

Apertures in the plate aligned with the channel means are provided for enabling plunger access to the flexible tubes in order to regulate fluid flow thereto. More particularly, in accordance with the present invention, two of the plurality of flexible tubes may be disposed in the channel means in a generally parallel relationship with one another and a cutout portion in the plate may be provided for enabling a pump head to be disposed within an outside envelope of a reusable cartridge.

In conjunction therewith, the channel means may comprise a channel for supporting one of the plurality of flexible tubes in an arcuate fashion across the cutout for engaging the pump head. In addition, a cavity may be provided in the plate with fluid communication with one of the plurality of flexible tubes along with a pressure sensitive element and diaphragm for suspending the pressure sensitive element over the cavity. This arrangement enables the monitoring of pressure of the flexible tube.

A hinged member provides means for removably sealing the diaphragm means and the pressure sensitive element across the cavity, while at the same time enabling operative access to the pressure-sensing element. More specifically, the hinged member is arranged for peripheral sealing of the diaphragm against a cavity parameter.

In addition, header means may be provided disposed in a spaced apart relationship along one or more of the plurality of flexible tubes for preventing lateral movement of the tubes within a channel means. Specifically, the header may also couple a pair of tubes which may be disposed in a parallel fashion to the plate.

In one embodiment of the present invention, a pressure-sensing element may comprise a ferromagnetic disk. Alternatively, the pressure-sensing element may include a laser light reflector or an ultrasonic reflector responsive, by concomitant movement with the fluid in the cavity, for sensing pressure differential which is translated into an electrical signal corresponding thereto.

Importantly, the major elements of the present invention, namely, the plate and the hinged member are autoclavable, i.e., capable of being sterilized with conventional autoclaving equipment so that the reusable cartridge assembly may be repeatedly used.

BRIEF DESCRIPTION OF THE DRAWINGS

The advantages and features of the present invention will be better understood by the following description when considered in conjunction with the accompanying drawings in which:

FIG. 3 is an exploded perspective view of the cartridge assembly in accordance with one embodiment of the present invention;

FIG. 4 is a perspective view of a second plate showing fluid flow channels therein;

FIG. 5 is an exploded perspective view of an alternative embodiment of the present invention in which a gasket includes conduits therein for the flow of fluids therethrough;

FIG. 7 is a plan view of the embodiment shown in FIG. 6;

FIG. 8 is a section view taken along the line 8—8 in FIG. 7; and

FIG. 9 is a section view taken along the line 9—9 in FIG. 7.

DETAILED DESCRIPTION

Figure 1:
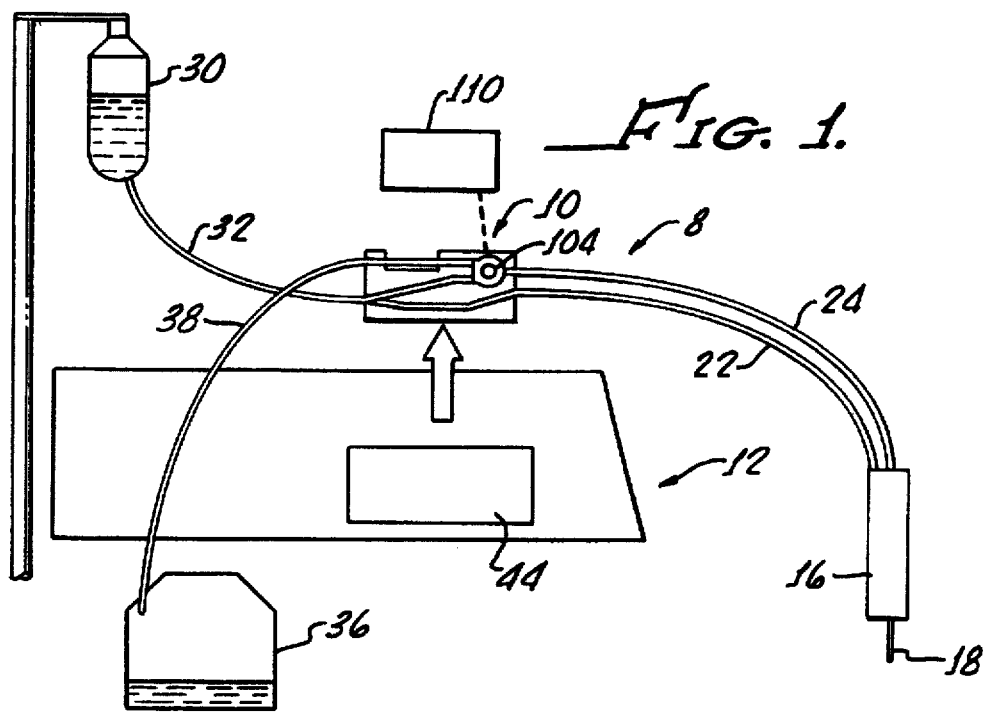
FIG. 1 is a schematic representation of the present invention illustrating its use with a surgical instrument, a saline solution supply, and a waste receptacle.

In FIG. 1, there is shown, in a conceptual format, a surgical instrument system 8, a drawer-loading reusable cartridge assembly 10, a control cabinet 12 having a pump head 14 (see FIG. 2), and a surgical instrument 16 (see FIG. 1).

Figure 2:
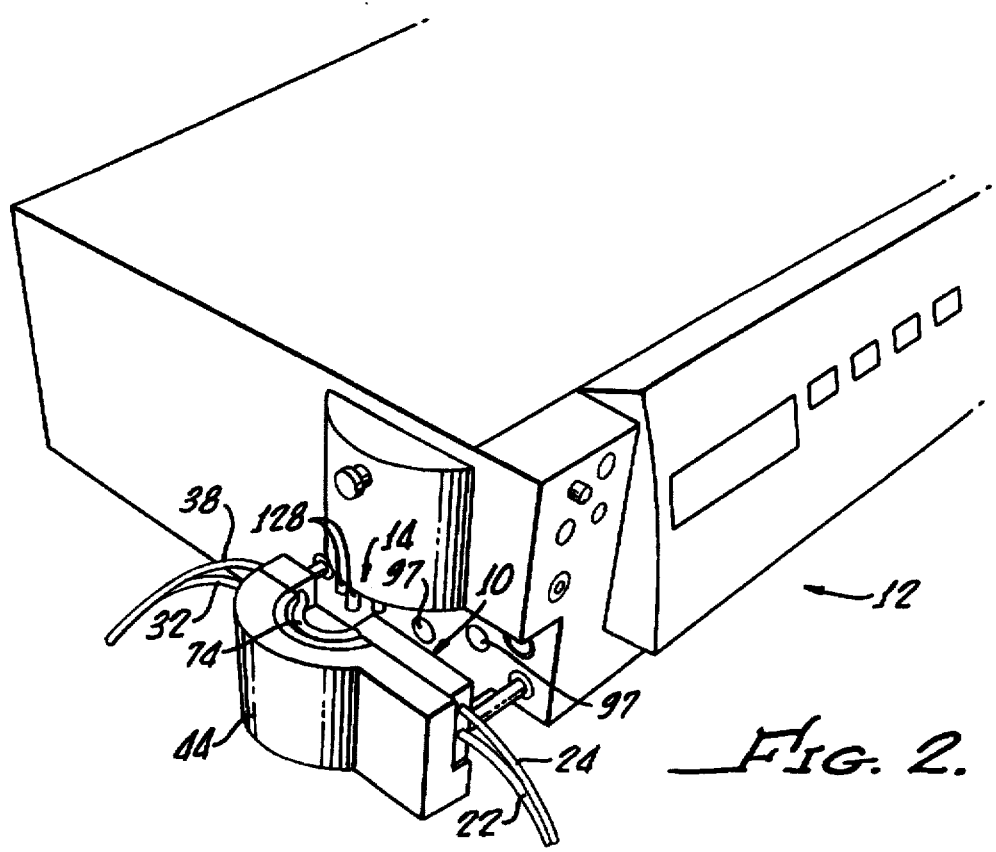
FIG. 2 is a perspective view of a cartridge assembly as it may be inserted into a drawer and control cabinet.

As hereinabove described, the present invention is used in conjunction with the surgical instrument or handpiece 16 for ophthalmic surgery, requiring irrigation and aspiration of fluids. As will be hereinafter discussed in greater detail, the reusable cartridge assembly 10 is connected with an irrigation line 22 and an aspiration line 24 for providing fluid communication between the surgical handpiece 16 and a source 30 of balanced saline solution (BSS) through a BSS line 32 and also with a waste receptacle 36 through a waste line 38. All these are diagrammatically represented in FIG. 1. As will be described hereinafter in greater detail, the reusable cartridge assembly or cassette cartridge 10 is sized for insertion into a drawer 44 in the cabinet 12 (FIG. 2).

Turning now to FIG. 3, the reusable cartridge assembly, or cartridge, 10 in accordance with the present invention for use in the control cabinet, or the machine, 12 generally includes the first plate 48 which is routed, or grooved to provide a means defining a plurality of flow channels 50 therein, the channels being in fluid communication with nipples 52 disposed on edges 54, 56 of the first plate 48.

A sealing gasket 58 includes a sheet 60 formed from a suitable autoclavable flexible material, provides a means for sealing against the first plate 48 to prevent the fluid from leaving the flow channels 50.

A second plate 62 provides a means for applying a sealing pressure between the sheet 60 and the first plate 48. Alignment between the first plate 48, the gasket 58 and the second plate 62 is provided by pins 64 protruding from a first plate 48 and corresponding holes 66 in the sheet 60 and holes 68 in the second plate 62. The first plate 48 and second plate 62 with the gasket 58 disposed therebetween may be held in a sealing and abutting relationship by any means such as clips 70 or pin snaps 72 for engaging the pins 64. The clamping means shown is only a specific example with any suitable means for holding the first plate 48, gasket 58 and second plate 62 being acceptable.

A tube 74 communicating with the sealing gasket 58 enables engagement between the tube 74 and the pump head 12, as hereinafter described in greater detail, for causing circulation of fluid through the flow channels 50.

As shown in FIG. 4, the second plate 62 may include flow channels 76 for enabling fluid to pass from the flow channels 50 in the first plate through holes 78 in the sheet 60 into the channels 76 and thereafter in and out of the tube 74 by holes 80 in the sheet 60.

Flow in the channels 50 may be controlled by plate portions 82, 84 and apertures 86, 88 and holes 90, 92 in the second plate 60, which may be sealed by membranes 94, 96 for enabling plungers 97 (see FIG. 2) to effect elation of fluid through the channels 50 by pressing portions 96, 98 against the plate portions 82, 84 to regulate or stop fluid flow in the channels 50. An arrangement similar to this is shown in U.S. Pat. Nos. 4,735,610 and 4,758,238.

Importantly, the first plate 48 is formed with a cavity 100 having a back surface 102 which is in fluid communication with the flow channels 50 for establishing a volume of fluid, and the gasket 58 includes a sensing element 104 suspended in a planar relationship therewith by a diaphragm 106 so that changes in the pressure of fluid within the cavity 100 cause the sensing element 104 and diaphragm to move in a direction perpendicular to the plane of the sheet 60 in order to provide a means for measuring the pressure of the fluid within the channels 50.

The sensing element 104 may be a ferromagnetic disk which is coupled to a measuring device 110 (see FIG. 1) which may be a transducer as described in U.S. patent application Ser. No. 07/893,119, filed Feb. 25, 1994. This reference is incorporated herewith by this reference thereto for teaching the manner in which the ferromagnetic disk may be coupled to a force transducer.

Alternatively, the sensing element 104 may be a laser light reflector or an ultrasound reflector and the measuring element 110 correspondingly may be a laser detector or ultrasound detector.

Turning now to FIG. 5, an alternative embodiment 110 in accordance with the present invention generally includes a first plate 112 which is routed, or grooved, to provide a means defining a plurality of flow channels 114, 116 which are in fluid communication with nipples 120, 122 disposed on edges 130, 132 of the first plate 112. In addition, grooves 134, 136 may be provided for accommodating conduits 138, 140 formed in a gasket sheet 146. The conduits 138, 140 may be integrally formed into the gasket 146 or adhered thereto in a manner providing for protrusion of the conduits 138, 140 on either side of the sheet gasket 146 for acceptance into the channels 134, 136 of the first plate and channels 148, 150 in a second plate 152. The conduits 138 may terminate in mini manifolds 154, 156 which are sized for acceptance into indentations 160, 162 in the first plate 112 and 166, 168 in the second plate 152.

The second plate 152 provides means for providing a sealing pressure to the sheet 146 and the first plate 112. Alignment between the first plate 112, the gasket 146 and the second plate 152 is provided by pins 170 protruding from the first plate and corresponding holes 172 in the sheet 146 and holes 176 in the second plate 152. The first plate 116 and second plate 152 may be held in a sealing and abutting relationship by any means such as clips 180 or pin snaps 182 or engagement pins 170. Openings 184 in the second plate provide a means for enabling plunger 97 access to the gasket conduits 138, 140 in order to regulate fluid flow therein by forcing same against berms 86, 88 formed in the grooves 134, 136 respectively.

A tube 190 communicating with the sealing gasket 146 enables engagement between the tube 190 and the pump head 12, as hereinbefore described in connection with embodiment 10. It should be noted that while the tube 74 may be fixed to the gasket 58 as shown in FIG. 3, alternatively, the tube 190 may be separate from the gasket 146 but in communication therewith when tube 190 ends are held in alignment with the gasket 190 by the first plate 112, and the second plate 152.

Similar to the embodiment 10, the second plate 152 may include flow channels 192 for enabling fluid to pass from flow channels 114, 116 in the first plate 112 through holes 194 in the sheet 146 into the channels 192 and thereafter in and out of the tube 190 by holes 196 in the sheet 146.

Similar to the embodiment shown in FIG. 3, the first plate 112 of the second embodiment 110 is formed with a cavity 200 having a back surface 202 which is in fluid communication with the flow channels 114 for establishing a volume of fluid, and the gasket 148 includes a sensing element 204 suspended in a planar relationship therewith by a diaphragm 206 so that changes in the pressure of fluid within the cavity 200 cause a sensing element 204 and diaphragm 206 to move in a direction perpendicular to the plane of the sheet 146 in order to provide a means for measuring the pressure of the fluid within the channels 114.

As hereinbefore described, the sensing element 204 may be a ferromagnetic disk, a laser-like reflector, or an ultrasound reflector.

Figure 6:
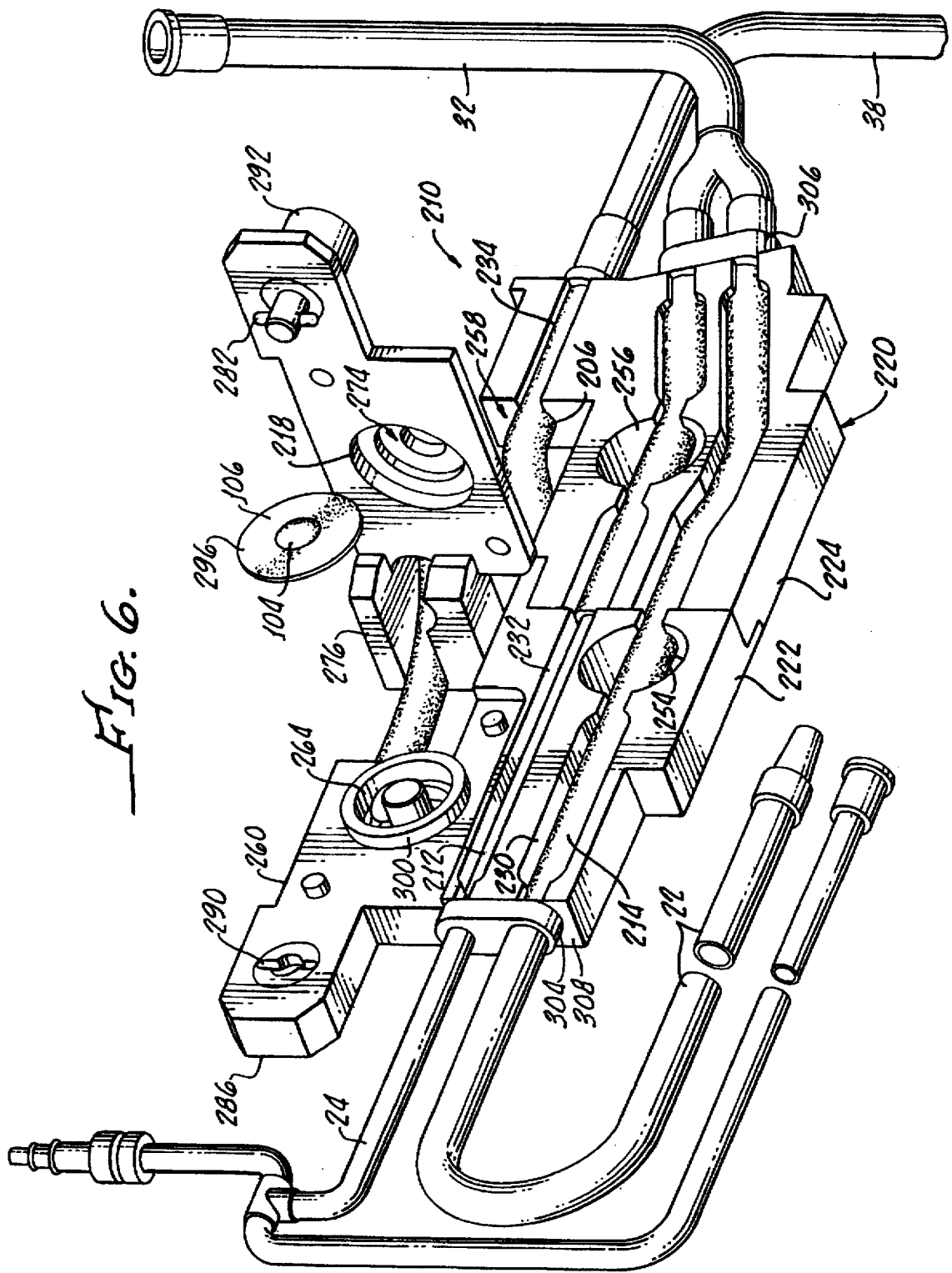
FIG. 6 is a perspective view of yet another embodiment of the present invention.

Turning now to FIG. 6 there is shown an alternative embodiment of a reusable cartridge assembly 210 in accordance with the present invention. It should be appreciated that the cartridge 210 is compatible with the control cabinet 12, pump head 14, handpiece 16, and plungers 97, all shown in FIGS. 1 and 2. It should be appreciated that comparable numerical references throughout the figures of this application refer to identical or substantially similar parts.

In general, the reusable cartridge assembly 210 for the phaco machine 12 generally includes a plurality of flexible tubes 212, 214, 216 for the handling of irrigation and aspiration fluids through the cassette 210, as hereinbefore shown and described, along with a plate 220 which may comprise two separable portions 222, 224, interconnected in any conventional manner. It should be appreciated that the plate 220 may be formed from a single piece of material such as, for example, stainless steel. Importantly, channels 230, 232, 234 are formed in the plate 220 which provide a means for supporting and removably holding the flexible tubes 212, 214, 216 within the plate 220.

As more clearly shown in FIGS. 8 and 9, the tube 214 is disposed within the channel 232 above a face 238 on the plate 220. Thus, no interference is possible with the tube when inserted into the phaco machine 12 (see FIG. 2). The structure providing this feature includes a bore 242 in the plate which includes a lateral opening 244 extending between the bore 242 and the plate face 238. Preferably, the cross section of the bore 242 is circular in order to accommodate the tube 232 therein with the bore 242 in an outside diameter of the tube 214 having approximately the same diameter. As shown in FIGS. 7–9, the lateral opening 244 may include a narrow portion 248 which provides specific means for removably holding the tube 214 within the channel 232. The narrow portion 248 having a width smaller than a diameter of the tube 214. It should be appreciated that while only one of the plurality of the channels 230, 232, 234 is discussed with reference to the support of the tube 232 therein, the structure throughout the plate 220 provides for a number of channels 230, 232, 234 with bores, lateral openings having narrow portions therein are not separately described for the sake of clarity.

Additionally, apertures 254, 256 formed in the plate 220 and aligned with the channels 232, 234 provide a means for enabling plunger 97 (see FIG. 2) access to the flexible tubes 220, 224, in order to regulate fluid flow therethrough.

As shown in FIGS. 6 and 7, a cutout portion 258 in plate 220 enables the pump head 14 (see FIG. 2) to be disposed within an outside envelope or perimeter 260 of the plate 220 to form engagement with the tube 216 (see FIG. 6). The tube 216 is supported by the channel 234 in an arcuate fashion across the cutout 258 for engaging the head 14.

A cavity 264 formed in the plate 220 is in fluid communication with the tube 216 contacted by the pump head 14 shown by the inlet 268 and outlet 270 to cavity 264. As most clearly shown in FIG. 7, a pressure-sensing element 104 hereinbefore described is suspended within the diaphragm 106 and a hinged lid 274 is provided for removably sealing a diaphragm 106 and pressure-sensing element 104 across the cavity 264 while at the same time enabling operative access to the pressure-sensing element 104. The lid includes a hinge 276 having an opening 278 in the lid 274 for providing access to the sensor 104 when the lid 274 is in a closed position with a locking pin 282 engaging a bottom 286 to plate 220 through a hole 290 aligned with the locking pin 282. The locking pin 282 is rotatably mounted in the lid 272 276 in a conventional manner and rotatable by a connected thumb screw 292. Sealing of the diaphragm 106 along a periphery 296 is enabled by a protruding cavity perimeter 300.

Additionally, headers 304, 306 formed in the tubes 214, 216 in a spaced apart relationship for engagement with ends 308, 310 of the plate 220 provides a means for preventing lateral movement of the tubes 214, 216 within the channels 232, 234.

As shown in FIG. 6, the headers 304, 306 may be disposed along and connecting two of the tubes 212, 214.

Although there has been hereinabove described a reusable cartridge assembly for a phaco machine, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A reusable cartridge assembly for a phaco machine, said reusable cartridge assembly comprising:
   a plurality of flexible tubes for handling of irrigation and aspiration fluids to and from a handpiece;
   a plate;
   a channel means, formed in said plate, for supporting and removably holding the flexible tubes within said plate, said channel means including bores through said plate and lateral openings extending between the bores and a face of said plate, said lateral openings including means, defining narrow portions, for removably holding the plurality of tubes, each of said narrow portions having a width smaller than a diameter of a corresponding tube disposed in a corresponding bore; and
   means, defining apertures in said plate and aligned with said channel means for enabling plunger access to the flexible tubes, extending across the apertures, in order to regulate fluid flow therethrough.

2. The reusable cartridge assembly according to claim 1 wherein said bores are generally circular in cross section.

3. The reusable cartridge assembly according to claim 1 wherein said two of the plurality of flexible tubes are disposed in said channel means in a generally parallel relationship with one another.

4. The reusable cartridge assembly according to claim 3 further comprising means, including a cutout portion in said plate, for enabling a pump head to be disposed within an outside envelope of the reusable cartridge.

5. The reusable cartridge assembly according to claim 4 wherein said channel means comprises a channel for supporting one of the plurality of flexible tubes in an arcuate fashion across said cutout for engaging said pump head.

6. The reusable cartridge assembly according to claim 5 further comprising means defining a cavity in said plate, said cavity being in fluid communication with said one of the plurality of flexible tubes.

7. The reusable cartridge assembly according to claim 6 further comprising a pressure-sensing element and diaphragm means for suspending the pressure-sensing element over said cavity.

8. The reusable cartridge assembly according to claim 7 further comprising means for removably sealing said diaphragm means and pressure-sensing element across said cavity and for enabling operative access to the pressure-sensing element.

9. The reusable cartridge assembly according to claim 8 wherein said means for removably sealing said diaphragm and pressure-sensing element comprises a hinged member means for peripheral sealing of said diaphragm against a cavity perimeter.

10. The reusable cartridge assembly according to claim 9 wherein the pressure-sensing element comprises a laser light reflector.

11. The reusable cartridge assembly according to claim 9 wherein the pressure-sensing element comprises a ferromagnetic disk.

12. The reusable cartridge assembly according to claim 9 wherein the pressure-sensing element comprises an ultrasound reflector.

13. The reusable cartridge assembly according to claim 9 wherein said diaphragm means surrounds said pressure-sensing element.

14. The reusable cartridge assembly according to claim 1 further comprising header means, disposed in a spaced apart relationship along at least one of the plurality of flexible tubes, for preventing lateral movement of at least one of the plurality of flexible tubes in said channel means.

15. The reusable cartridge assembly according to claim 14 wherein said header means is disposed along a pair of the plurality of flexible tubes.

16. The reusable cartridge assembly according to claim 15 wherein said pair of the plurality of flexible tubes is disposed in said channel means in a generally parallel relationship with one another.

17. The reusable cartridge assembly according to claim 16 further comprising means, including a cutout portion in said plate, for enabling a pump head to be disposed within an outside envelope of the reusable cartridge.

18. The reusable cartridge assembly according to claim 17 wherein said channel means comprises a channel for supporting one of the plurality of flexible tubes in an arcuate fashion across said cutout for engaging said pump head.

19. The reusable cartridge assembly according to claim 18 further comprising means defining a cavity in said plate, said cavity being in fluid communication with said one of the plurality of flexible tubes.

20. The reusable cartridge assembly according to claim 19 further comprising a pressure-sensing element and diaphragm means for suspending the pressure-sensing element over said cavity.

21. The reusable cartridge assembly according to claim 20 further comprising means for removably sealing said diaphragm means and pressure-sensing element across said cavity and for enabling operative access therewith.

22. The reusable cartridge assembly according to claim 21 wherein said means for removably sealing said diaphragm and pressure-sensing element comprises a hinged member means for peripheral sealing of said diaphragm against a cavity perimeter.

* * * * *